(12) United States Patent
Dumont

(10) Patent No.: US 10,427,127 B2
(45) Date of Patent: Oct. 1, 2019

(54) DISCONNECTOR DEVICE

(71) Applicant: GE Healthcare Limited, Buckinghamshire (GB)

(72) Inventor: Philippe Dumont, Loncin (BE)

(73) Assignee: GE HEALTHCARE LIMITED, Buckinghamshire (GB)

( * ) Notice: Subject to any disclaimer, the term of this patent is extended or adjusted under 35 U.S.C. 154(b) by 110 days.

(21) Appl. No.: 15/547,011

(22) PCT Filed: Mar. 16, 2016

(86) PCT No.: PCT/EP2016/055704
§ 371 (c)(1),
(2) Date: Jul. 27, 2017

(87) PCT Pub. No.: WO2016/146693
PCT Pub. Date: Sep. 22, 2016

(65) Prior Publication Data
US 2018/0021750 A1    Jan. 25, 2018

(30) Foreign Application Priority Data

Mar. 16, 2015   (GB) .................................. 1504409.2

(51) Int. Cl.
*B01J 19/00* (2006.01)
*C07B 59/00* (2006.01)

(52) U.S. Cl.
CPC ......... *B01J 19/0093* (2013.01); *B01J 19/004* (2013.01); *C07B 59/00* (2013.01); *B01J 2219/00799* (2013.01); *B01J 2219/00813* (2013.01); *B01J 2219/00822* (2013.01); *B01J 2219/00833* (2013.01); *B01J 2219/00867* (2013.01); *B01J 2219/00873* (2013.01);
(Continued)

(58) Field of Classification Search
None
See application file for complete search history.

(56) References Cited

U.S. PATENT DOCUMENTS

| 2006/0245980 | A1 | 11/2006 | Kiselev et al. |
| 2010/0031486 | A1* | 2/2010 | Catlin ................. F16L 37/0982 29/237 |
| 2011/0150714 | A1* | 6/2011 | Elizarov .............. B01J 19/0093 422/159 |
| 2013/0170931 | A1 | 7/2013 | Samper et al. |

FOREIGN PATENT DOCUMENTS

| EP | 1803805 A1 | 7/2007 |
| WO | 2012170602 A1 | 12/2012 |

(Continued)

OTHER PUBLICATIONS

International Search Report and the Written Opinion of the International Searching Authority, or the Declaration from International Appl. No. PCT/EP2016/055704, dated Jul. 12, 2016.
(Continued)

*Primary Examiner* — Jennifer A Leung
(74) *Attorney, Agent, or Firm* — Arent Fox, LLP

(57) ABSTRACT

The present invention relates to an automated radiosynthesis device adapted for enhanced automatic disconnection of a disposable kit once a radiosynthesis has been carried out. The automated radiosynthesis device of the invention therefore reduces the time to remove the disposable kit from the radiosynthesis device and reduces radiation exposure to the operator.

19 Claims, 2 Drawing Sheets

(52) U.S. Cl.
CPC ............... *B01J 2219/00891* (2013.01); *B01J 2219/00894* (2013.01); *B01J 2219/00918* (2013.01); *B01J 2219/00927* (2013.01); *B01J 2219/00952* (2013.01); *B01J 2219/00961* (2013.01); *B01J 2219/00986* (2013.01); *C07B 2200/05* (2013.01)

(56) References Cited

FOREIGN PATENT DOCUMENTS

| WO | 2013012813 A1 | 1/2013 |
| WO | 2013049608 A2 | 4/2013 |
| WO | 2016146693 A1 | 9/2016 |

OTHER PUBLICATIONS

Great Britain Search Report from GB Appl. No. GB1504409.2, dated Aug. 17, 2015.
Zelterberg, Uno, "A Change in Usage of Cyclotrons for Medical Isotope Production," GE Healthcare, Mar. 25, 2015, 24 pages, [accessed online] https://indico.cern.ch/event/366464/contribution/13/attachments/728654/999810/A_change_in_usage_cyclotrons_for_medical_web.pdf.
China First Office Action corresponding to CN Application No. 201680016201.8, dated Apr. 18, 2019.
China Search Report corresponding to CN Application No. 201680016201.8, dated Apr. 8, 2019.

* cited by examiner

DISCONNECTOR DEVICE

TECHNICAL FIELD OF THE INVENTION

The present invention relates to the synthesis of radiolabelled compounds. In particular, the present invention relates to an apparatus for the automated synthesis of radiolabelled compounds, especially radiotracer compounds.

DESCRIPTION OF RELATED ART

Radiolabelled compounds for use as in vivo imaging agents are currently typically prepared by means of an automated synthesis apparatus (alternatively "radiosynthesiser" or "radiosynthesis device"). Such automated synthesis apparatuses are commercially available from a range of suppliers, including: GE Healthcare; CTI Inc. (USA); Ion Beam Applications S.A., Belgium; Raytest (Germany) and Bioscan (USA). The radiochemistry takes place in a "cassette" or "cartridge" designed to fit removably and interchangeably onto the apparatus, in such a way that mechanical movement of moving parts of the apparatus controls the operation of the cassette. Suitable cassettes may be provided as a kit of parts that is assembled onto the apparatus in a number of steps, or may be provided as a single piece that is attached in a single step, thereby reducing the risk of human error. The single piece arrangement is generally a disposable single use cassette which comprises all the reagents, reaction vessels and apparatus necessary to carry out the preparation of a given batch of radiopharmaceutical.

Once synthesis of the radiopharmaceutical is finished the synthesiser can be set-up for the next production, by removing the used cassette and mounting a new cassette. As the used cassette is contaminated with residues of radioactive compounds, the cassette has to be removed and discarded to a shielded waste container as quickly as possible to reduce radiation exposure to operator. Known cassette-based radiosynthesisers are often equipped with means to disconnect and release the cassette from the radiosynthesiser with no or limited operator intervention. For example a cassette drawer can be used as the means used to interface the cassette (single-use fluid path) with the radiosynthesiser. The operator inserts the cassette into the drawer and activates the drawer by pushing two buttons simultaneously. The connection of the cassette to the device may be achieved by movement of the drawer towards the radiosynthesiser's front panel. In a similar fashion, disconnection of the cassette from the radiosynthesiser is achieved by movement of the drawer away from the synthesiser's front panel. U.S. Pat. No. 7,235,216 refers to a mechanism whereby a used kit is automatically ejected and then dropped into a prepared receptacle in order to install a fresh cassette before waiting for the radioactivity to decay. Also, WO 2013/012 mentions automatic ejection of a cassette into a shielded waste container. Systems are therefore known comprising means to disconnect and release the cassette from the synthesiser with no or limited operator intervention.

The present inventors recognise some problems with the known configurations. Firstly, that disconnection of the cassette from lines leading for example to the product collection vial or in the case of $^{18}$F synthesis to the $^{18}$O-water recovery vial remains a manual step entailing radiation exposure to the operator. Furthermore, where there is a luer lock connection of the outlet line to an extension line leading to the product collection vial in a neighbouring hot cell. Disconnection of these lines requires manual operation in front of an open hot cell while there is still radiation present from the previous run.

SUMMARY OF THE INVENTION

In one aspect the present invention provides an automated radiosynthesis device (1) comprising:
(i) a plurality of connectors for removably attaching a disposable kit (3) to said automated radiosynthesis device (1);
(ii) automated attachment means for automated attachment to and removal from said automated radiosynthesis device (1) of said disposable kit (3);
(iii) a disconnector device (5) comprising a rigid substantially planar body (5a) defining an aperture (5b) therethrough;
(iv) plurality of actuators to selectively control moving parts of said disposable kit (3);
(v) a control unit for directing the selective control of the moving parts of said disposable kit (3) by said plurality of actuators;
(vi) a reaction vessel heating well;
(vii) an inert gas conduit;
(viii) a vacuum conduit; and,
(ix) a radioisotope conduit.

In another aspect the present invention provides a radiosynthesis method comprising:
(a) providing an automated radiosynthesis device (1) of the invention;
(b) attaching a disposable kit (3) as defined herein to said automated radiosynthesis device (10) wherein said disposable kit (3) comprises at least one line having a connector at the end distal to the disposable kit (3);
(c) connecting said at least one line to a respective vial;
(d) carrying out a radiosynthesis on said attached disposable kit (3);
(e) disconnecting said disposable kit (3) following said step (c) wherein said disconnecting includes disconnecting said at least one line from its respective vial by means of a disconnector device (5) as defined herein.

The present invention permits facile disconnection of a disposable kit from an automated synthesis device. The method of the invention is readily amenable to automation and therefore can be achieved without any manual intervention thereby reducing radiation dose to the user. Once the kit is disconnected it can be placed into a shielded container to allow the radioactivity thereon to decay away from the interior of the hot cell. In this way the interior of the hot cell comprises a reduced amount of remaining radioactivity at an earlier point in time following a radiosynthesis.

DETAILED DESCRIPTION OF THE PREFERRED EMBODIMENTS

Figure 1:
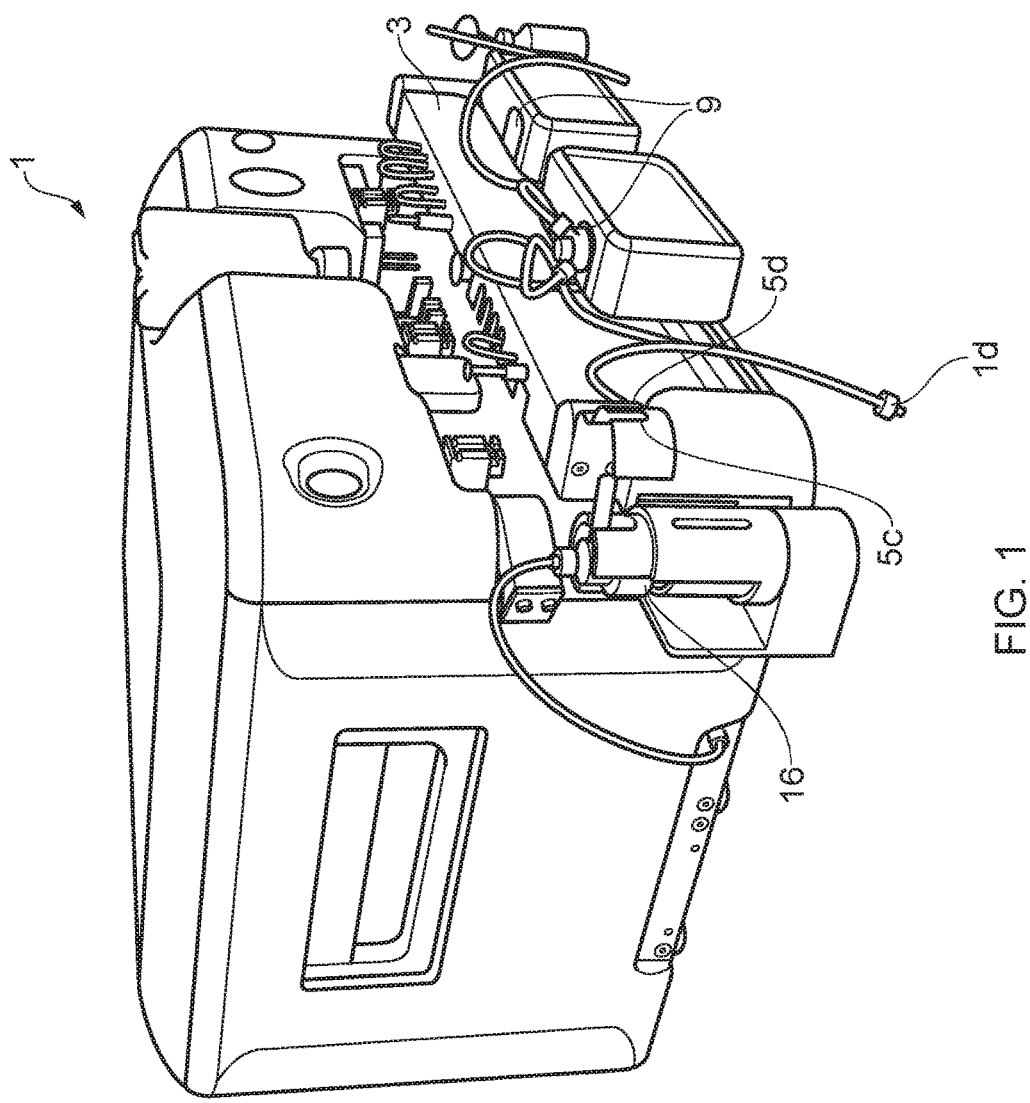
FIG. 1 shows an exemplary radiosynthesis device of the present invention showing a disconnection device on the cassette drawer.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "automated radiosynthesis device" (also referred to herein as "radiosynthesis device") as used herein refers to an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Such automated radiosynthesisers are commercially available from a range of suppliers (Satyamurthy et al, above), including: GE Healthcare; CTI Inc (USA); Ion Beam Applications S. A. (Belgium); Raytest (Germany) and Bioscan (USA). Automated radiosynthesis devices are designed to be employed in a suitably configured radioactive work cell, or "hot cell", which provides suitable radiation shielding to protect the operator from potential radiation dose, as well as ventilation to remove chemical and/or radioactive vapours. Using a cassette the automated radiosynthesis device has the flexibility to make a variety of different radiopharmaceuticals with minimal risk of cross-contamination, by simply changing the cassette. This approach also has the advantages of simplified set-up hence reduced risk of operator error, improved GMP (good manufacturing practice) compliance, multi-tracer capability, rapid change between production runs, pre-run automated diagnostic checking of the cassette and reagents, automated cross-check (e.g. using a barcode or radio-frequency identification) of chemical reagents vs. the synthesis to be carried out, reagent traceability, single-use and hence no risk of cross-contamination, tamper and abuse resistance. The radiosynthesis device is programmed to operate pumps, syringes, valves, heating element, and controls the provision of nitrogen and application of vacuum to the disposable kit so as to direct the source fluid into mixing with the reagents, performing the chemical reactions, through the appropriate purification cartridges, and selectively pumping the output tracer and waste fluids into appropriate vial receptacles outside the disposable kit. While the fluid collected in the output vial is typically input into another system for either purification and/or dispensement, the radiosynthesis device and disposable kit can also be connected to a separate purification system which returns a purified compound back to the disposable kit for further processing.

Each of the "connectors" of the automated radiosynthesis device of the present invention represents one half of a pair of mating connectors or fasteners where the other half is present at a corresponding location on the disposable kit. In one embodiment of the automated radiosynthesis device of the invention said plurality of connectors is selected from the group comprising fasteners and fluidic connectors. In one embodiment of the automated radiosynthesis device of the invention said fluidic connectors are selected from the group comprising push-on type connectors, luer slip connectors and luer screw connectors.

The term "disposable kit" herein refers either to a kit of parts or to a cassette. A "kit of parts" comprises first and second end valves and a plurality of interior valves oriented along a flowpath therebetween. Such a kit includes a reaction vessel adapted to be connected to one or more of the valves, at least one pump means supported on a valve, at least one reagent vial holding contents which are directable into the flowpath, wherein the reagent vial adapted to be connected to said flowpath so that the contents may be directed into the flowpath. The kit further includes at least one cartridge adapted to be connected across at least one of the valves. The components of the kit of parts are provided separately and it is required that the user assemble them prior to use. In contrast, a "cassette" is a pre-assembled single-use piece of apparatus designed to fit removably and interchangeably onto an automated radiosynthesiser. A typical cassette has an elongate manifold including first and second end valves and a plurality of interior valves oriented along a manifold flowpath therebetween. The manifold defines an elongate manifold flowpath between each of the valves. The cassette includes a reaction vessel, at least one pump means (e.g. a syringe) supported on a valve, at least one reagent vial holding contents which are directable into the manifold flowpath, and at least one purification cartridge connected across at least one of the valves. The cassette is desirably adaptable for synthesizing clinical batches of different radiopharmaceuticals with minimal customer installation and connections. Connections between the cassette and the radiosynthesis device in one embodiment are automatically made to the reagent vials by driving the septums thereof onto penetrating spikes of the cassette so as to allow the synthesizer access to use the reagents.

In one embodiment of the automated radiosynthesis device of the invention said disposable kit is suitable for the synthesis of a radiotracer compound. A "radiotracer compound" is a biologically active chemical compound in which one or more atoms have been replaced by a radioisotope. Radiotracer compounds can be formulated for use in nuclear medicine, including single photon emission computed tomography (SPECT), positron emission tomography (PET) and scintigraphy. Such radiotracer compounds are well-known to those of skill in the art. In one embodiment said radiotracer compound is a PET tracer. In one embodiment said radiotracer compound is an $^{18}$F-labelled PET tracer. An "[$^{18}$F]-labelled PET tracer" is a chemical compound that comprises an $^{18}$F atom and is suitable for use as a PET tracer. Non-limiting examples of [$^{18}$F]-labelled PET tracers include [$^{18}$F]fluorodeoxyglucose ([$^{18}$F]FDG), [$^{18}$F]Fluoromisonidazole ([$^{18}$F]FMISO), [$^{18}$F]fluorothymidine ([$^{18}$F]FLT), [$^{18}$F]Fluoroazomycin arabinofuranoside ([$^{18}$F]FAZA), [$^{18}$F]Fluoroethyl-choline ([$^{18}$F]FECH), [$^{18}$F]fluorocyclobutane-1-carboxylic acid ([$^{18}$F]FACBC), [$^{18}$F]flumanezil ([$^{18}$F]FMZ), [$^{18}$F]tyrosine, [$^{18}$F]altanaserine, 4-[$^{18}$F]fluoro-3-iodobenzyl guanidine ([$^{18}$F]FIBG), meta-[$^{18}$F]fluorobenzylguanidine ([$^{18}$F]mFBG) and [$^{18}$F]5-fluorouracil.

The disposable kit in one embodiment is removably attached to a substantially planar face of said automated radiosynthesis device. The term "substantially planar face" refers to a surface or panel of the radiosynthesis device onto which the disposable kit is attached. The face and the disposable kit will suitably be in planar association with each other when the kit is attached.

The term "reagents for carrying out a radiosynthesis" refers to reactants and solvents required for a particular radiosynthesis reaction. There are many known radiosynthetic methods and the reader is referred for example to "Radiochemical Syntheses: Radiopharmaceuticals for Positron Emission Tomography" (Volume 1, 2001, Wiley, Scott & Hockley, Eds.) and to "Handbook of Radiopharmaceuticals: Radiochemistry and Applications" (2003, Wiley, Welch & Redvanly, Eds.) for discussion of the common general knowledge in the art of radiopharmaceuticals.

The term "automated attachment means" refers to the mechanism by which the disposable kit is attached in an automated fashion to the radiosynthesis device. In one embodiment of the automated radiosynthesis device of the invention said automated attachment means comprises a drawer into which said disposable kit can be loaded and wherein said drawer is moveable between a first position for loading/disconnecting said disposable kit and a second position where said loaded disposable kit is attached to said face of said automated radiosynthesis device.

The term "disconnector device" refers to a device configure to disconnect connectors present on lines coming off said disposable cassette. In one embodiment said disconnector device is made from metal or a rigid plastic. In one embodiment said metal is aluminium or stainless steel. In one embodiment said disconnector device is fixed to said automated attachment means. An example of such an embodiment is illustrated in FIG. 1, which shows a second generation FASTlab™ radiosynthesis device having a disconnection device (5) fixed to the cassette drawer. In FIG. 1 the line from the cassette (3) to the $^{18}$O-water recovery vial (16) is shown where the male part (1d) of the luer connector at the distal end of the line is disconnected from the female part of the luer connector on the $^{18}$O-water recovery vial (16). The cassette drawer is in the loading and/or disconnection position, i.e. the position prior to or following a radiosynthesis. Linear movement of the cassette drawer in a horizontal direction towards the synthesiser (1) brings the female part of the luer connector through the arms of the disconnector device (5), ultimately allowing the male part (1d) of the luer connector to be connected either manually or in an automated fashion. The male part (1d) of the luer connector will then be situated at the side of the disconnector device (5) facing away from the radiosynthesis device (1) so that, following the radiosynthesis, movement of the cassette drawer away from the radiosynthesis device (1) automatically pushes the male part (1d) of the luer connector away from the female part of the luer connector thereby disconnecting them. It is to be understood that the alternate arrangement of male to female is also possible.

Figure 2:
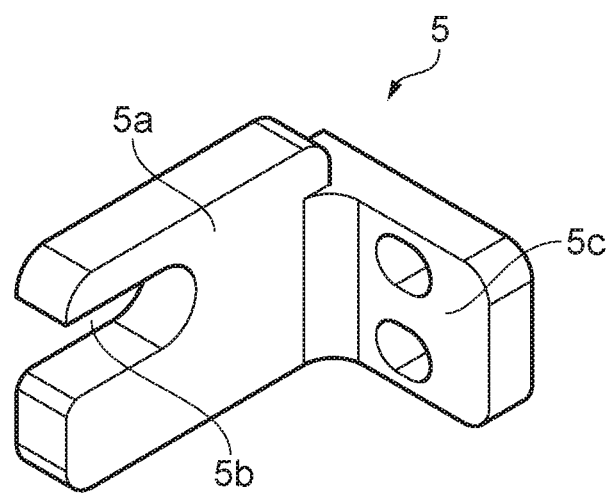
FIG. 2 illustrates an exemplary disconnection device of the present invention.

The term "rigid substantially planar body defining an aperture therethrough" is intended to encompass a number of suitable configurations. For example, in one exemplary embodiment, as illustrated in FIG. 1, the disconnector device (5) can be a fork having arms (or "prongs") (5c, 5d) spaced apart a distance slightly less than the maximum diameter of the male part (1d) of a luer connector. The space between the arms (5c, 5d) in such an embodiment can be understood to be the aperture (5b). It is envisaged that the arms (5c, 5d) can be substantially parallel and or may form a "V" shape. In another embodiment the aperture (5b) is substantially an "O" shape having a diameter slightly less than the maximum diameter of the male part (1d) of a luer connector. An exemplary disconnector device (5) of the invention is illustrated in FIG. 2, showing parallel arms (5a, 5b) at one end and at the other end means (5c) for connecting the device to the automated radiosynthesis device (1).

The term "actuators" refers to any suitable means to move or control parts of the disposable kit. An actuator is operated by a source of energy, typically electric current, hydraulic fluid pressure, or pneumatic pressure, and converts that energy into motion. In one embodiment of the automated radiosynthesis device of the present invention said plurality of actuators is selected from the group comprising rotatable arms for stopcocks of valves, linear actuators, arms that press onto reagent vials and pinch valves (e.g. solenoid pinch valves selectively blocking flow).

The term "moving parts" refers to those parts of the disposable kit that move in a controlled fashion by means of co-operative functional association with actuators on the radiosynthesis device. In one embodiment of the automated radiosynthesis device of the invention said moving parts of said disposable kit are selected from the group comprising reagent vials, syringes and valves.

The "control unit" of the radiosynthesis device of the present invention includes software for operating the disposable kit in accordance with a particular radiosynthesis method. The software comprises instructions for a particular radiosynthesis method to be carried out on said disposable kit attached to said automated radiosynthesis device. The software is provided as a non-transitory computer readable storage medium with an executable program for performing a particular radiosynthesis method when the appropriate disposable kit is mounted to radiosynthesis device.

The "reaction vessel heating well" of the radiosynthesis device of the invention is designed to receive a reaction vessel provided as part of the disposable kit so as to provide any heat required for chemical reactions occurring therein.

The "inert gas conduit", "vacuum conduit" and "radioisotope conduit" are suitably tubing linking the radiosynthesis device in a fluid-tight manner respectively to a source of inert gas (e.g. nitrogen), a vacuum (e.g. a pump) and a source of a radioisotope (e.g. a vial or the output line of a cyclotron). The conduits can comprise spigots to permit controlled delivery. The inert gas and vacuum assist in fluid transfer through the manifold and in operation of the disposable kit. The radioisotope conduit may extend from the source of the radioisotope to a delivery plunger.

The term "at least one line" refers to lines, suitably flexible polymeric tubing, forming part of a fluid-tight connection from the disposable kit to additional components outside said kit. The line may link the radiosynthesis device to a vial, a dispensing device or any other upstream or downstream processing apparatus.

Suitably, at either end of said line (i.e. proximal and distal to the disposable kit) there are fluid-tight connectors where the connectors are as defined hereinabove. In one embodiment the disconnection device acts on the connector present at the end of the line distal to said disposable kit. In one embodiment said line may further comprise an extension line leading, e.g. to another hot cell.

In one embodiment said connector is a luer connector.

In one embodiment said connector is at the end of the line distal to said disposable kit.

In one embodiment of the method of the present invention said at least one line is fluidly connected to a product collection vial.

In one embodiment of the method of the present invention said radiosynthesis is the radiosynthesis of a $^{18}$F-labelled compound as defined hereinabove. In this embodiment said at least one line is fluidly connected to a $^{18}$O-water recovery vial.

Features, integers, characteristics, compounds, chemical moieties or groups described in conjunction with a particular aspect, embodiment or example of the invention are to be understood to be applicable to any other aspect, embodiment or example described herein unless incompatible therewith.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. An automated radiosynthesis device comprising:
    a plurality of fluidic connectors for removably attaching a disposable kit to said automated radiosynthesis device;
    automated attachment means for automated attachment to and removal from said automated radiosynthesis device of said disposable kit;
    a disconnector device comprising a rigid substantially planar body defining an aperture therethrough, the disconnector device rigidly attached to the automated attachment means such that movement of the disposable kit away from the from the automated radiosynthesis device disconnects at least one fluidic connector;
    a plurality of actuators to selectively control moving parts of said disposable kit;
    a control unit for directing the selective control of the moving parts of said disposable kit by said plurality of actuators;
    a reaction vessel heating well;
    an inert gas conduit;
    a vacuum conduit; and
    a radioisotope conduit.

2. The automated radiosynthesis device as defined in claim 1, wherein said fluidic connectors include push-on connectors, luer slip connectors, luer screw connectors, or combinations thereof.

3. The automated radiosynthesis device as defined in claim 2, wherein the body of the disconnector device includes a fork with arms spaced apart by a distance slightly less than a maximum diameter of a male part of a luer connector.

4. The automated radiosynthesis device as defined in claim 2, wherein the aperture of the disconnector device has an O-shape with a diameter slightly less than a maximum diameter of a male part of a luer connector.

5. The automated radiosynthesis device as defined in claim 1, wherein said disposable kit is suitable for the synthesis of a radiotracer compound.

6. The automated radiosynthesis device as defined in claim 1, wherein said disposable kit is suitable for the synthesis of a $^{18}$F-labelled PET radiotracer compound.

7. The automated radiosynthesis device as defined in claim 1, wherein said disposable kit is a single-use cassette.

8. The automated radiosynthesis device as defined in claim 1, wherein said plurality of actuators include rotatable arms for stopcocks of valves, linear actuators, arms that press onto reagent vials, pinch valves, or combinations thereof.

9. The automated radiosynthesis device as defined in claim 1, wherein said moving parts of said disposable kit include reagent vials, syringes, valves or combinations thereof.

10. The automated radiosynthesis device as defined in claim 1, wherein said control unit includes software comprising instructions for a particular radiosynthesis method to be carried out on said disposable kit attached to said automated radiosynthesis device.

11. The automated radiosynthesis device as defined in claim 1, wherein said automated attachment means comprises a drawer into which said disposable kit can be loaded and wherein said drawer is moveable between a first position for loading and/or disconnecting said disposable kit and a second position where said loaded disposable kit is attached to said face of said automated radiosynthesis device.

12. The automated radiosynthesis device as defined as defined in claim 1, wherein the body of the disconnection device is configured to form rigid arms defining said aperture therebetween.

13. The automated radiosynthesis device as defined in claim 12, wherein said rigid arms are spaced apart at at least one point along their lengths a distance slightly less than the maximum diameter of a male part of a luer connector.

14. The automated radiosynthesis device as defined in as defined in claim 1, wherein said disconnector device is made from a metal or a rigid plastic.

15. A radiosynthesis method comprising:
    attaching the disposable kit to the automated radiosynthesis device of claim 1, wherein said disposable kit comprises at least one line having one of said fluidic connectors at the end distal to the disposable kit;
    connecting said at least one line to a respective vial;
    carrying out a radiosynthesis on said attached disposable kit;
    disconnecting said disposable kit following said connecting wherein said disconnecting includes disconnecting said at least one line from its respective vial by means of the disconnector device.

16. The radiosynthesis method as defined in claim 15, wherein said at least one line is connected to a product collection vial.

17. The radiosynthesis method as defined in claim 15, wherein said radiosynthesis is the radiosynthesis of a $^{18}$F-labelled compound.

18. The radiosynthesis method as defined in claim 15, wherein said at least one line is connected to a $^{18}$O-water recovery vial.

19. The radiosynthesis method as defined in claim 17, wherein said at least one line is connected to a product collection vial.

* * * * *